(12) United States Patent
Nakanishi

(10) Patent No.: US 11,202,763 B2
(45) Date of Patent: Dec. 21, 2021

(54) PHOSPHATIDYLCHOLINE TRANSDERMAL ABSORPTION PREPARATION

(71) Applicant: UNISH INC., Osaka (JP)

(72) Inventor: Hirofumi Nakanishi, Osaka (JP)

(73) Assignee: UNISH INC., Osaka (JP)

( * ) Notice: Subject to any disclaimer, the term of this patent is extended or adjusted under 35 U.S.C. 154(b) by 14 days.

(21) Appl. No.: 16/618,026

(22) PCT Filed: Apr. 27, 2018

(86) PCT No.: PCT/JP2018/017312
§ 371 (c)(1),
(2) Date: Nov. 27, 2019

(87) PCT Pub. No.: WO2019/150594
PCT Pub. Date: Aug. 8, 2019

(65) Prior Publication Data
US 2020/0138731 A1    May 7, 2020

(30) Foreign Application Priority Data

Jan. 31, 2018 (JP) .............................. JP2018-015574

(51) Int. Cl.
*A61K 9/70* (2006.01)
*A61K 31/685* (2006.01)
(Continued)

(52) U.S. Cl.
CPC .......... *A61K 9/7038* (2013.01); *A61K 31/685* (2013.01); *A61K 47/32* (2013.01); *A61K 47/44* (2013.01)

(58) Field of Classification Search
None
See application file for complete search history.

(56) References Cited

U.S. PATENT DOCUMENTS

| 2014/0303189 A1 | 10/2014 | Goto et al. |
| 2016/0256552 A1 | 9/2016 | Yamasaki |
| 2016/0339042 A1 | 11/2016 | Modi |

FOREIGN PATENT DOCUMENTS

| EP | 1852130 A1 | 11/2007 | |
| EP | 2142445 A1 * | 1/2010 | ......... B65D 83/0463 |

(Continued)

OTHER PUBLICATIONS

Christiansen (The health benefits of Lecithin, accessed online Feb. 5, 2021) (Year: 2021).*

(Continued)

*Primary Examiner* — Melissa S Mercier
(74) *Attorney, Agent, or Firm* — Masuvalley & Partners; Peter R. Martinez

(57) ABSTRACT

To provide a phosphatidylcholine transdermal absorption preparation containing phosphatidylcholine in an adhesive layer. A phosphatidylcholine transdermal absorption preparation has a configuration in which an adhesive layer formed on at least one side of a support contains phosphatidylcholine, an adhesive component, and a lipophilic component, and thus the preparation becomes a patch-type transdermal absorption preparation which acts as a fat-decreasing agent which contains phosphatidylcholine and can exert an effect that local obesity such as subcutaneous fat is dissolved and fat is decreased by transdermal absorption of phosphatidylcholine as the preparation is pasted to the skin of a human body since phosphatidylcholine can be stably present in the adhesive layer and has an advantage due to the patch dosage form that the preparation can be fixed to the affected area and is more favorably handled as compared to liquid preparations and the like.

10 Claims, 1 Drawing Sheet

(51) Int. Cl.
*A61K 47/32* (2006.01)
*A61K 47/44* (2017.01)

(56) References Cited

FOREIGN PATENT DOCUMENTS

| EP | 2143445 | A1 | * | 1/2010 | ............. | A61K 47/14 |
|----|---------|----|---|--------|---|----------|
| EP | 2143445 | A1 | | 1/2010 | | |
| EP | 2471539 | A1 | * | 7/2012 | ................ | A61P 3/04 |
| EP | 2906199 | A1 | | 8/2015 | | |
| IT | VR20070150 | A1 | | 4/2009 | | |
| IT | VR20070150 | A1 | * | 4/2009 | | |
| JP | S5747820 | A | | 3/1982 | | |
| JP | S5955819 | A | | 3/1984 | | |
| JP | H083069 | A | | 1/1996 | | |
| JP | 2005531595 | A | | 10/2005 | | |
| JP | 2007509085 | A | | 4/2007 | | |
| JP | 2017-154989 | A | | 9/2017 | | |
| KR | 2014-0143938 | A | | 12/2014 | | |
| WO | 2006090839 | A1 | | 8/2006 | | |
| WO | 2008133272 | A1 | | 11/2008 | | |
| WO | 2011024354 | A1 | | 3/2011 | | |
| WO | WO 2013/027681 | A1 | | 2/2013 | | |
| WO | WO 2014/058427 | A1 | | 4/2014 | | |

OTHER PUBLICATIONS

Dictionary.com definition of liquid paraffin; accessed online Feb. 8, 2021. (Year: 2021).*
International Search Authority/JPO, International Search Report dated Jun. 19, 2018 in International Patent Application No. PCT/JP2018/017312 (with English translation), 4 pages.
Aviram Spernath et al., "Phosphatidylcholine embedded micellar systems: Enhanced permeability through rat skin", Journal of Colloid and Interface Science, Nov. 19, 2007, vol. 318, p. 421-429, 9 pages.
EPO, Extended European Search Report dated Feb. 16, 2021 in European Application No. EP 18904440.7, 11pages.
JPO, Japanese Office Action dated Feb. 2, 2021 in Japanese Application No. 2019-508997, with English translation 6 pages.

* cited by examiner

PHOSPHATIDYLCHOLINE TRANSDERMAL ABSORPTION PREPARATION

RELATED APPLICATIONS

This application is the U.S. National Phase application under 35 U.S.C. § 371 of International Patent Application No. PCT/JP2018/017312, international filing date Apr. 27, 2018, which claims priority to Japanese Patent Application No. 2018-015574 filed on Jan. 31, 2018, which are hereby expressly incorporated by reference in their entireties for all purposes.

TECHNICAL FIELD

The present invention relates to a phosphatidylcholine transdermal absorption preparation. More specifically, the present invention relates to a patch-type transdermal absorption preparation containing phosphatidylcholine in an adhesive layer.

BACKGROUND ART

Phosphatidylcholine, which is a main component of soybean lecithin obtained from soybean seed extract oil, is used in cosmetics and pharmaceuticals as surfactants (emulsifiers and the like) and skin conditioning agents. Such phosphatidylcholines are amphiphilic and thus can penetrate fat cells and phosphatidylic acid such as phosphatidylcholine can participate in the activation of fatty acid release pathways through which the local obesity such as subcutaneous fat is decreased, and thus these can be expected to exert the effect of dissolving subcutaneous fat.

As a means for decreasing obesity with excessive fat (fat layer) among subcutaneous fat accumulation and obesity, for example, a method in which a composition for removing subcutaneous accumulation of fat is directly subcutaneously injected has been adopted, and phosphatidylcholine preparations and the like have been used as such a composition (see, for example, Patent Literature 1). However, subcutaneous injection of such phosphatidylcholine preparations is problematic in terms of pain and safety at the time of treatment, thus the development of a transdermal absorption-type preparation (transdermal absorption preparation. It is also called transdermal administration preparation.) of which self-administration is possible but direct subcutaneous injection is not required has been expected. Hence, a transdermal composition which contains natural product-derived phosphatidylcholine, L-carnitine, propylene glycol, glycerin, and water but does not contain a lipophilic base has been provided (see, for example, Patent Literature 2).

CITATION LIST

Patent Literature

Patent Literature 1: JP 2007-509085 A
Patent Literature 2: JP 5747820 B2

SUMMARY OF INVENTION

Technical Problem

It is also demanded to provide a transdermal absorption preparation which contains phosphatidylcholine in the adhesive layer and has a patch dosage form. As the preparation is produced as a transdermal absorption preparation which contains phosphatidylcholine in the adhesive layer and has a patch dosage form, the preparation becomes a preparation which is a transdermal absorption type but is not a type to be applied to the skin, also has an advantage due to the patch dosage form that the preparation can be fixed to the affected area by being pasted to the affected area at which fat is considered to be decreased, and moreover is more favorably handled as compared to liquid and gel preparations. However, it has been difficult to produce preparations in a patch dosage form by the configurations of preparations provided so far, such as the configuration disclosed in Patent Literature 2 above.

The present invention has been made in view of the problems and an object thereof is to provide a patch-type phosphatidylcholine transdermal absorption preparation containing phosphatidylcholine in an adhesive layer.

Solution to Problem

In order to solve the above problems, a transdermal absorption preparation according to the present invention is a transdermal absorption preparation which includes a support, and an adhesive layer formed on at least one side of the support, and is characterized in that the adhesive layer contains phosphatidylcholine, an adhesive component, and a lipophilic component.

The transdermal absorption preparation according to the present invention is characterized in that the adhesive component is a styrene-based thermoplastic elastomer in the above-described present invention.

The transdermal absorption preparation according to the present invention is characterized in that carnitine is further contained in the above-described present invention.

The transdermal absorption preparation according to the present invention is characterized in that a content of phosphatidylcholine is 2.5% to 8.0% by mass with respect to an entire adhesive layer in the above-described present invention.

The transdermal absorption preparation according to the present invention is characterized in that the lipophilic component contains mineral oil in the above-described present invention.

The transdermal absorption preparation according to the present invention is characterized in that a branched polyolefin is further contained in the above-described present invention.

The transdermal absorption preparation according to the present invention is characterized in that the branched polyolefin is a hydrogenated C6-14 olefin polymer in the above-described present invention.

Advantageous Effects of Invention

The phosphatidylcholine transdermal absorption preparation according to the present invention has a configuration in which the adhesive layer formed on at least one side of the support contains phosphatidylcholine, an adhesive component, and a lipophilic component. Hence, the preparation becomes a patch-type transdermal absorption preparation which acts as a fat-decreasing agent which contains phosphatidylcholine and can exert an effect that local obesity such as subcutaneous fat is dissolved and fat is decreased by transdermal absorption of phosphatidylcholine as the preparation is pasted to the skin and the like of a human body and the like since phosphatidylcholine can be stably present in the adhesive layer in addition to an advantage due to the patch dosage form that the preparation can be fixed to the affected area and is more favorably handled as compared to liquid preparations and the like.

DESCRIPTION OF EMBODIMENTS (I) Configuration of Transdermal Absorption Preparation 1

Figure 1:
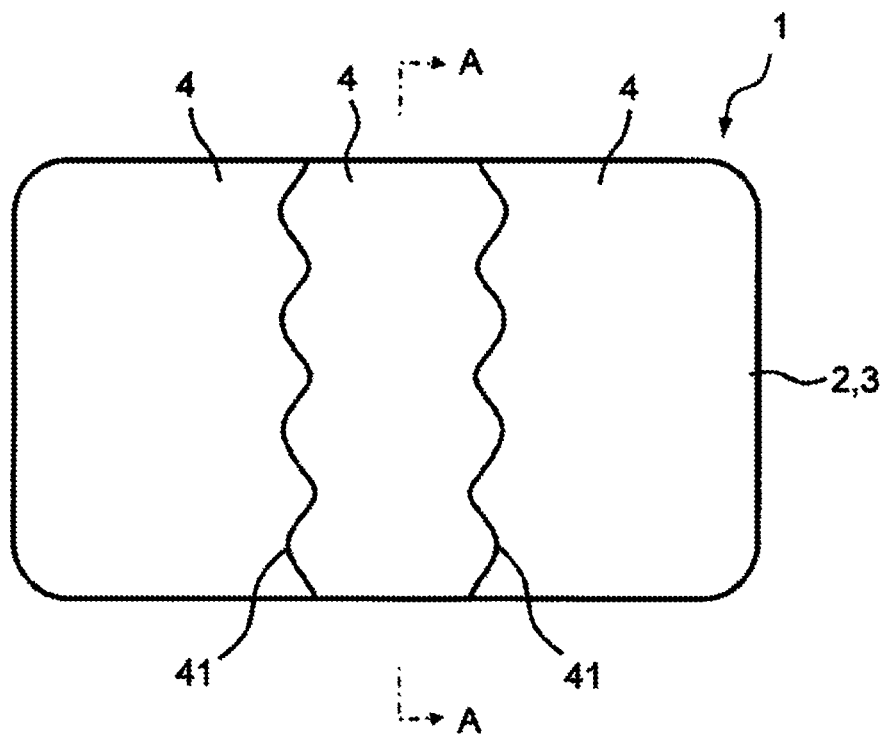
FIG. 1 is a front view illustrating an aspect of a transdermal absorption preparation according to the present invention.
Figure 2:
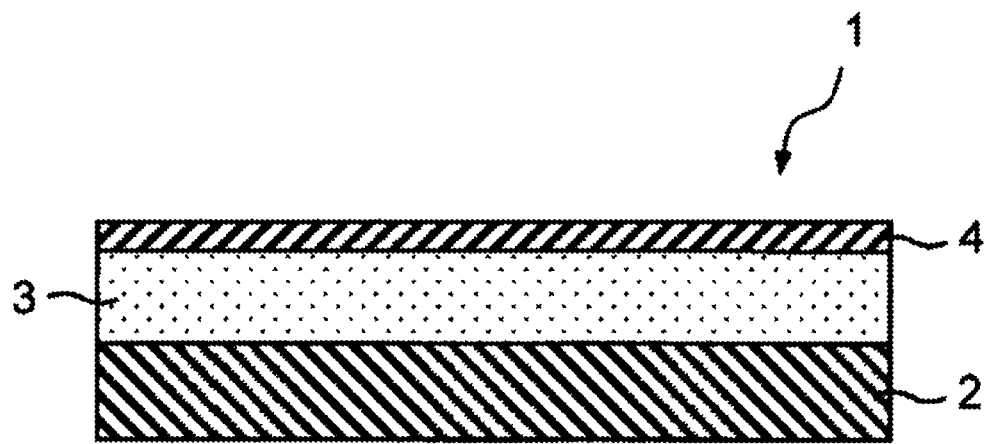
FIG. 2 is a cross-sectional view taken along A-A in FIG. 1.

Hereinafter, an aspect of a phosphatidylcholine transdermal absorption preparation 1 according to the present invention will be described. FIG. 1 is a front view illustrating an aspect of the transdermal absorption preparation 1 according to the present invention, and FIG. 2 is a cross-sectional view taken along A-A in FIG. 1. In the drawings, 1 denotes a phosphatidylcholine transdermal absorption preparation (transdermal absorption preparation), 2 denotes a support, 3 denotes an adhesive layer, 4 denotes a release sheet, and 41 denotes a cut, respectively.

The phosphatidylcholine transdermal absorption preparation (transdermal absorption preparation) 1 according to the present invention is a transdermal absorption preparation 1 which include a support 2 and an adhesive layer 3 formed on at least one side of the support 2 and has a configuration in which the adhesive layer 3 contains phosphatidylcholine, an adhesive component, and a lipophilic component. Incidentally, in FIGS. 1 and 2, a configuration in which the adhesive layer 3 is formed on one side of the support 2 and the release sheet 4 is pasted to the surface of the adhesive layer 3 is illustrated as an example of the configuration of the transdermal absorption preparation 1.

(II) Support 2:

In the present invention, the support 2 is not particularly limited as long as those generally used as an application for support of a patch which is the transdermal absorption preparation 1 can be used, and examples thereof include stretchable or non-stretchable woven fabric and nonwoven fabric formed of polyethylene, polypropylene and the like, films or sheets (in the present invention, "film" and "sheet" are synonymous with each other. The same applies hereinafter.) of polyolefins such as polyethylene and polypropylene, polyesters such as polyethylene terephthalate (PET) and polyethylene naphthalate (PEN), ethylene-vinyl acetate copolymer, vinyl chloride and the like, or a foamed sheet of urethane, polyurethane and the like (these are also referred to as a "sheet-like material" in some cases). Those described above may be used singly or in combination (mixture or lamination) of two or more kinds thereof. Incidentally, in order to prevent accumulation of static electricity on the support 2, an antistatic agent and the like may be contained in the above-described sheet-like materials such as woven fabric and nonwoven fabric and the like that constitute the support 2.

The thickness of the support 2 in the transdermal absorption preparation 1 is, for example, preferably 200 to 280 μm and particularly preferably about 240 to 260 μm but is not particularly limited to this range.

In addition, the transdermal absorption preparation 1 of the present invention may adopt a configuration in which the adhesive layer 3 is sandwiched between the support 2 and the release sheet 4 as illustrated in FIGS. 1 and 2. As the release sheet 4, a release sheet 4 generally used in the field of patches can also be equipped. As the release sheet 4, for example, resin sheets of polyolefins such as polyethylene and polypropylene, polyesters such as polyethylene terephthalate (PET) and polyethylene naphthalate (PEN), and polystyrene, glassine paper, an aluminum sheet, a foamed polyethylene sheet, or a foamed polypropylene sheet and the like, or any laminate composed of two or more kinds thereof can be used. In addition, those obtained by subjecting these to silicone processing, fluororesin processing, embossing, hydrophilic processing, hydrophobic processing and the like can be used.

The thickness of the release sheet 4 is, for example, preferably 80 to 120 μm and particularly preferably 90 to 110 μm but is not particularly limited to this range.

Incidentally, in order to facilitate peeling off from the adhesive layer 3, it is preferable to form a cut (slit) 41 on the release sheet 4, and the configuration illustrated in FIG. 1 shows an aspect in which two curved cuts 41 are formed and the release sheet 4 is divided into three.

(III) Adhesive Layer 3:

The adhesive layer 3 contains phosphatidylcholine, an adhesive component, and a lipophilic component. Phosphatidylcholine (also described as phosphatidylcholine) is often referred to generically as a phospholipid having a structure in which choline forms a phosphate ester bond as a hydrophilic moiety of glycerophospholipid and two fatty acids of the glycerol skeleton forms an ester bond as a hydrophobic moiety. Phosphatidylcholine is a main component of soybean lecithin obtained from soybean seed extract oil, participates in the activation of fatty acid release pathways through which the local obesity such as subcutaneous fat is decreased by penetrating into fat cells, and thus exerts an effect of dissolving subcutaneous fat. Incidentally, phosphatidylcholine has different phospholipid names depending on the choice of two fatty acids and is called divalmitoyl phosphatidylcholine in a case in which two palmitic acids are selected as fatty acids, DL phosphatidylcholine in a case in which two linoleic acids are selected as fatty acids, divalmitoylphosphatidylcholine in a case in which two palmitic acids are selected as fatty acids, and PO phosphatidylcholine in a case in which palmitic acid and oleic acid are selected as fatty acids.

Examples of the phosphatidylcholine include conventionally known egg yolk phosphatidylcholine, soybean phosphatidylcholine, egg yolk lysophosphatidylcholine, soybean lysophosphatidylcholine, hydrogenated egg yolk phosphatidylcholine, hydrogenated soybean phosphatidylcholine, hydrogenated egg yolk lysophosphatidylcholine, and hydrogenated soybean lysophosphatidylcholine. These may be used singly or in combination of two or more kinds thereof.

The content of phosphatidylcholine in the adhesive layer 3 is preferably 1.0% to 9.0% by mass with respect to the entire adhesive layer 3 (this indicates that the entire mass of the adhesive layer 3 is taken as 100% by mass. The same applies hereinafter.) By setting the content of phosphatidylcholine to be in such a range, the preparation can efficiently exert an effect of decreasing local obesity such as subcutaneous fat by transdermal absorption of phosphatidylcholine as a patch-type transdermal absorption preparation. The content of phosphatidylcholine is particularly preferably 2.5% to 8.0% by mass with respect to the entire adhesive layer 3.

Incidentally, carnitine may be added to phosphatidylcholine. By the presence of carnitine, the stability and the like of phosphatidylcholine in the adhesive layer 3 can be enhanced and the effect attained by containing phosphatidylcholine is more efficiently exerted. Here, examples of carnitine include L-carnitine, DL-carnitine, and acetyl-L-carnitine, these may be used singly or in combination of two or more kinds thereof. In the present invention, it is preferable to use L-carnitine. In addition, an inner salt, an inorganic salt such as hydrochloride or sodium salt, an organic acid salt such as a tartrate, an oxalate, or a fumarate, and the like may be used as carnitine.

With regard to the amount of carnitine added with respect to phosphatidylcholine, the amount of carnitine added is preferably 8.5 to 12.0 parts by mass and particularly preferably 9.0 to 10.5 parts by mass in a case in which phosphatidylcholine is taken as 100 parts by mass.

Next, as the adhesive component forming the adhesive layer 3, it is preferable to use, for example, a thermoplastic elastomer. Here, the "thermoplastic elastomer" is generally a generic term for elastomers which exhibit thermoplasticity to be softened and exhibit fluidity by heating but to return to a rubber-like elastic body by cooling. Examples of such thermoplastic elastomers include styrene-based, urethane-based, acrylic-based, and olefin-based thermoplastic elastomers. In the present invention, it is preferable to use styrene-based thermoplastic elastomers (including hydrogenated styrene-based thermoplastic elastomers) which can exhibit both sufficient skin adhesiveness and low skin irritation as well as can allow phosphatidylcholine to be stably present in the adhesive layer 3 and it is particularly preferable to use styrene-based copolymers (including hydrogenated ones) such as styrene-based block copolymers.

Specific examples of the styrene-based block copolymers (including hydrogenated ones. The same applies hereinafter.) as a thermoplastic elastomer include a styrene-butadiene block copolymer, a hydrogenated styrene-butadiene block copolymer, a styrene-butadiene-styrene block copolymer, a hydrogenated styrene-butadiene-styrene block copolymer, a styrene-isoprene block copolymer, a hydrogenated styrene-isoprene block copolymer, a styrene-isoprene-styrene block copolymer, and a hydrogenated styrene-isoprene-styrene block copolymer. Moreover, examples thereof include a styrene-ethylene/butylene block copolymer, a styrene-ethylene/butylene-styrene block copolymer, a styrene-ethylene/propylene block copolymer, a styrene-ethylene/propylene-styrene block copolymer, a styrene-isobutylene block copolymer, a styrene-isobutylene-styrene block copolymer, and hydrogenated block copolymers of these. These styrene-based block copolymers may be used singly or in combination of two or more kinds thereof.

Incidentally, in the above, the description of "ethylene/butylene" indicates a copolymer block composed of ethylene and butylene and the description of "ethylene/propylene" indicates a copolymer block composed of ethylene and propylene.

Among the above-mentioned styrene-based block copolymers, it is preferable to use at least one selected from the group consisting of a styrene-butadiene block copolymer, a hydrogenated styrene-butadiene block copolymer, a styrene-isoprene block copolymer, a hydrogenated styrene-isoprene block copolymer, a styrene-isoprene-styrene block copolymer, and a hydrogenated styrene-isoprene-styrene block copolymer from the viewpoint of being easily available and exhibiting favorable handleability as well as exhibiting both favorable skin adhesiveness and low skin irritation.

In addition, as the styrene-butadiene block copolymer (including hydrogenated one), a copolymer having a styrene component content of 5% to 55% by mass is preferable and a copolymer having a styrene component content of 10% to 50% by mass is particularly preferable. Moreover, those having a weight average molecular weight (the same applies hereinafter for the weight average molecular weight) of 10,000 to 5,500,000 as measured by gel filtration chromatography and the like are preferable and those having a weight average molecular weight of 15,000 to 500,000 are particularly preferable.

In addition, as the styrene-isoprene block copolymer (including hydrogenated one), a copolymer having a styrene component content of 5% to 55% by mass is preferable and a copolymer having a styrene component content of 10% to 50% by mass is particularly preferable. Moreover, those having a weight average molecular weight of 10,000 to 5,500,000 are preferable and those having a weight average molecular weight of 15,000 to 500,000 are particularly preferable.

Furthermore, as the styrene-isoprene-styrene block copolymer (including hydrogenated one), a copolymer having a styrene component content of 5% to 65% by mass is preferable and a copolymer having a styrene component content of 10% to 60% by mass is particularly preferable. Moreover, those having a weight average molecular weight of 18,000 to 5,500,000 are preferable and those having a weight average molecular weight of 20,000 to 500,000 are particularly preferable.

The content of the adhesive component such as the thermoplastic elastomer in the adhesive layer 3 is preferably 20.0% to 35.0% by mass with respect to the entire adhesive layer 3. It is not preferable that the content of the adhesive component is less than 20.0% by mass since there is a case in which the shape of the adhesive layer 3 is hardly maintained, and it is not preferable that the content of the adhesive component exceeds 35.0% by mass since there is a case in which the adhesiveness to the skin is insufficient. The content of the adhesive component such as the thermoplastic elastomer in the adhesive layer 3 is particularly preferably 25.0% to 30.0% by mass with respect to the entire adhesive layer 3.

Incidentally, for the purpose of enhancing the hardness and transparency of the adhesive layer 3 and improving the feel of use and mixing, dispersion and the like of the respective components of the adhesive layer 3, it is preferable to blend a branched polyolefin. Examples of such a polyolefin include a hydrogenated C6-14 olefin polymer, polybutene, hydrogenated polyisobutene, isoparaffins such as (C7,8)isoparaffin, (C8,9)isoparaffin, (C9-11) isoparaffin, (C10-13)isoparaffin, (C11,12)isoparaffin, (C11-13)isoparaffin, (C13,14)isoparaffin, (C13-16)isoparaffin, and (C18-70) isoparaffin, olefin oligomers, and hydrogenated polydecene. Among these, a hydrogenated C6-14 olefin polymer, polybutene, and hydrogenated polyisobutene are particularly preferable from the viewpoint of usability such as transparency and adhesive property of the adhesive layer 3. These may be used singly or in combination of two or more kinds thereof.

The content of the branched polyolefin in the adhesive layer 3 is preferably 2.0% to 15.0% by mass and particularly preferably 4.0% to 10.0% by mass with respect to the entire adhesive layer 3.

In addition, the lipophilic component is an effective component for forming the above-described phosphatidylcholine and adhesive component into the adhesive layer 3 in the present invention, and examples thereof include vegetable oil such as olive oil (olive fruit oil), orange oil (orange fruit oil), and mineral oil, animal oil, and mineral oil. By containing mineral oil among these and the following lipophilic components, the effect of transdermally absorbing phosphatidylcholine can be efficiently exerted.

Furthermore, examples of the lipophilic component include fatty acids such as palmitic acid, oleic acid, and stearic acid; vegetable oils such as avocado oil, linseed oil, almond oil, perilla oil, kaya oil, rapeseed oil, olive oil, corn oil, castor oil, safflower oil, sunflower oil, cottonseed oil, jojoba oil, macadamian nut oil, wheat germ oil, soybean oil, peanut oil, coconut oil, palm oil, palm kernel oil, camellia oil, and evening primrose oil; animal oils such as mink oil, fish oil, lard, and tallow; hydrocarbons such as liquid paraffin, squalene, squalane, polybutene, and hydrogenated polyisobutene; esters such as diisobutyl adipate, 2-hexyldecyl adipate, di-2-heptylundecyl adipate, N-alkyl glycol monoisostearate, isocetyl isostearate, trimethylolpropane triisostearate, cetyl 2-ethylhexanoate, ethylene glycol di-2-ethylhexanoate, neopentyl glycol di-2-ethylhexanoate, glyceryl tri-2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearatel, dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, and diisostearyl malate; silicones such as dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, and fluorine-modified polysiloxane; fluorine-based oil solutions such as perfluorodecane, perfluorooctane, and perfluoropolyether. The lipophilic components mentioned above may be used singly or in combination of two or more kinds thereof.

The content of the lipophilic component in the adhesive layer 3 is set to preferably 30.0% to 85.0% by mass, still more preferably 40.0% to 75.0% by mass, and particularly preferably 40% to 60% by mass with respect to the entire adhesive layer 3.

In the adhesive layer 3 having the above-described configuration, an antioxidant, a plasticizer, a filler, a drug dissolution auxiliary, an antibacterial agent, a skin irritation diminishing agent, an excipient and the like can be appropriately blended as an arbitrary component if necessary in a range in which the object and effect of the present invention are not affected.

The antioxidant is not particularly limited, and examples thereof include ascorbic acid derivatives such as ascorbyl palmitate and ascorbyl tetraisopalmitate, chelating agents such as sodium edetate, sodium sulfite, butylhydroxyanisole, butylhydroxytoluene, tocopherol and tocopherol derivatives such as tocopherol and tocopherol acetate, and quinoline and quinoline derivatives such as oxyquinoline sulfate.

The plasticizer is not particularly limited, and examples thereof include glycols such as ethylene glycol, diethylene glycol, triethylene glycol, propylene glycol, polyethylene glycol, and polypropylene glycol; oils and fats such as olive oil, castor oil, squalene, lanolin; hydrocarbons such as liquid paraffin; fatty acid esters such as diisopropyl adipate, diisobutyl adipate, benzyl benzoate, cetyl 2-ethylhexanoate, oleyl oleate, decyl oleate, benzyl acetate, diisopropyl sebacate, diethyl sebacate, sorbitan trioleate, sorbitan tristearate, cetyl palmitate, octyldodecyl myristate, cetyl myristate, myristyl myristate, and isopropyl myristate. These may be used singly or in combination of two or more kinds thereof.

The filler is not particularly limited, and examples thereof include kaolin, bentonite, and titanium dioxide. In addition, the drug dissolution auxiliary is not particularly limited, and examples thereof include cyclodextrins such as α-cyclodextrin, β-cyclodextrin, and γ-cyclodextrin (can also be used as excipients to be described later). The antibacterial agent is not particularly limited, and examples thereof include benzalkonium chloride, benzoic acid, and methyl parahydroxybenzoate. The skin irritation diminishing agent is not particularly limited, and examples thereof include anhydrous silicic acid. The excipient is not particularly limited, and examples thereof include cyclodextrin, lactose, and a cellulose-based powder (excipients such as cyclodextrin are usually used by being mixed with carnitine and the like in advance).

In order to obtain the transdermal absorption preparation 1 of the present invention, for example, among the components constituting the adhesive layer 3, phosphatidylcholine, the adhesive component such as a thermoplastic elastomer, and components to be added if necessary are each mixed with or dispersed in the lipophilic component and mixed or dispersed in a solvent such as acetone, ethyl acetate, or toluene if necessary to prepare a coating liquid for forming the adhesive layer 3. Subsequently, the coating liquid obtained is applied to the surface on which the adhesive layer 3 is to be formed of the support 2, and then dried (the solvent is scattered in the case of being mixed and the like in a solvent), whereby the transdermal absorption preparation 1 can be produced. The thickness of the adhesive layer 3 is preferably about 150 to 300 μm after drying.

Moreover, in the case of using the release sheet 4, the release sheet 4 is pressure-bonded to the adhesive layer 3 after being applied to the support 2 and the adhesive layer 3 can be thus laminated by being sandwiched between the support 2 and the release sheet 4. Alternatively, the coating liquid for the adhesive layer 3 may be applied onto the release sheet 4 and dried to scatter the solvent and thus to form the adhesive layer 3 on the surface of the release sheet 4 and then the support 2 may be bonded onto the adhesive layer 3 by pressure bonding.

The coating liquid for forming the adhesive layer 3 can be applied using, for example, conventionally known coaters such as a roll coater, a die coater, a gravure roll coater, a reverse roll coater, a kiss roll coater, a dip roll coater, a bar coater, a knife coater, and a spray coater. In addition, the coating liquid is dried preferably at a temperature of about 40° C. to 160° C., for example.

As described above, the phosphatidylcholine transdermal absorption preparation 1 according to the present invention has a configuration in which the adhesive layer 3 formed on at least one side of the support 2 contains phosphatidylcholine, an adhesive component, and a lipophilic component. Hence, the preparation becomes a patch-type transdermal absorption preparation a which acts as a fat-decreasing agent which contains phosphatidylcholine and can exert an effect that local obesity such as subcutaneous fat is dissolved and fat is decreased by transdermal absorption of phosphatidylcholine as the preparation 1 is pasted to the skin and the like of a human body and the like since phosphatidylcholine can be stably present in the adhesive layer 3 in addition to an advantage due to the patch dosage form that the preparation can be fixed to the affected area and is more favorably handled as compared to liquid preparations and the like.

Incidentally, as the phosphatidylcholine transdermal absorption preparation 1 of the present invention adopts a configuration in which the preparation is produced as a patch using the adhesive layer 3 containing a lipophilic component instead of a hydrophilic component, phosphatidylcholine which is a drug is favorably transdermally absorbed through the skin and this penetration mechanism is considered as follows.

In other words, it is presumed that this is because as the transdermal absorption preparation 1 which is a patch is pasted to the skin, phosphatidylcholine penetrates from the surface (sebum membrane) of the skin to the deep part of the skin (skin) in order by the skin concentration gradient. Moreover, the transpiration of moisture in the stratum corneum of the skin is suppressed and the polymer such as a thermoplastic elastomer which is an adhesive component becomes soft (plasticization of polymer) as well as the stratum corneum swells by the occlusive dressing therapy (ODT) effect due to the lipophilic component in addition to the support 2, thus the passage of phosphatidylcholine through the skin becomes favorable and transdermal absorption of phosphatidylcholine proceeds in a state of exhibiting enhanced skin penetrability.

Furthermore, with regard to the mechanism of transdermal absorption, low molecular weight components pass through the stratum corneum, but polymer components are different from the low molecular weight components, and inner wall cells of pores existing on the skin surface such as sweat glands and hair follicles are the main permeation pathways. Low molecular weight components diffuse in the lipophilic base (adhesive layer 3) and the stratum corneum, are distributed into the epidermis, then diffuse in the dermis, and are absorbed into cells and capillaries. However, polymer components diffuse in the lipophilic base and the pores, are distributed into the inner wall cells of the pores, and reach the dermis layer without passing through stratum corneum. In the present invention, it is considered that the stratum corneum swells by the occlusive dressing therapy effect of a lipophilic component and the like, thus diffusion in the pores is promoted and the permeation efficiency of the active component is improved.

The transdermal absorption preparation 1 according to the present invention can be expected to have an effect of dissolving local obesity such as subcutaneous fat and decreasing fat by transdermal absorption of phosphatidylcholine and is used by being pasted to the (skin of) affected area at which subcutaneous fat of a human body and the like is desired to be decreased. Incidentally, the frequency of pasting the transdermal absorption preparation 1 can be appropriately determined depending on the content of phosphatidylcholine and the like and the kinds and contents of other components in the adhesive layer 3, but it is considered that the effect is efficiently exerted by briefly pasting the preparation about 3 to 6 times a week (not particularly limited to this range).

It should be noted that the aspect described above shows an aspect of the present invention and the present invention is not limited to above-described embodiment, and it is needless to say that modifications and improvements in the range of being equipped with the configuration of the present invention and being able to achieve the object and effect of the present invention are included in the contents of the present invention. Moreover, it is not problematic even when the specific structure, shape, and the like when carrying out the present invention are other structures, shapes, and the like in the range in which the object and effect of the present invention can be achieved. The present invention is not limited to the respective embodiments described above, and modifications and improvements in the range in which the object and effect of the present invention can be achieved are included in the present invention.

For example, in the above-described embodiment, the configuration of the transdermal absorption preparation 1 has been described through an aspect in which two curved cuts 41 are formed on the release sheet 4 as illustrated in FIG. 1, but the shape of the cut 41 is arbitrary and the cut 41 may not be formed. In addition, only the support 2 and the adhesive layer 3 may be used and the release sheet 41 may not be used.

In the above-described embodiment, as an example of the configuration of the transdermal absorption preparation 1, a configuration in which the adhesive layer 3 is formed on one side of the support 2 and the release sheet 4 is pasted to the surface of the adhesive layer 3 has been described with reference to FIGS. 1 and 2, but the adhesive layer 3 may be formed on both sides of the support 2 or the release sheet 4 may be pasted to the surface of the adhesive layer 3 if necessary.

In the above-described embodiment, the shape of the transdermal absorption preparation 1 has been described by taking a substantially rectangular shape with four rounded corners as an example, as illustrated in FIG. 1, but the shape of the transdermal absorption preparation 1 that is a patch is arbitrary, and arbitrary shapes such as a polygonal shape such as a triangular shape, a quadrangular shape, or a pentagonal shape, a circular shape, an elliptical shape, or a geometric shape can be adopted. In addition, the size of the transdermal absorption preparation 1 is also arbitrary and can be appropriately determined depending on the place to which the preparation is pasted. In the case of a substantially rectangular shape (quadrangular shape) as illustrated in FIG. 1, one side (before being rounded in a case in which the four corners are rounded) may be set to, for example, about 50 to 200 mm, but the size is not particularly limited to this range.

In addition, the specific structure, shape and the like when carrying out the present invention may be other structures and the like in the range in which the object of the present invention can be achieved.

EXAMPLES

Hereinafter, the present invention will be described in more detail based on Examples and Reference Examples, but the present invention is not limited to these.

Example 1, Example 2, and Reference Example 1

Production of Transdermal Absorption Preparation:

Transdermal absorption preparations, which were a patch having the configuration illustrated in FIGS. 1 and 2, were produced by the following method. Incidentally, the compositions (components and contents (% by mass)) of the adhesive layers of Example 1, Example 2, and Reference Example 1 are presented in Table 1. Moreover, the numerical values (contents) in Table 1 are the values (% by mass) of the respective components in a case in which the entire adhesive layer is taken as 100% by mass. Incidentally, Reference Example 1 does not contain phosphatidylcholine.

(Composition of Components)

TABLE 1

| | | (Content: % by mass) | | |
|---|---|---|---|---|
| | Component | Example 1 | Example 2 | Comparative Example 1 |
| 1 | Phosphatidylcholine | 5.0 | 2.0 | — |
| 2 | Hydrogenated styrene-butadiene block copolymer | 8.0 | 8.0 | 8.0 |
| 3 | Styrene-isoprene block copolymer | 19.0 | 19.0 | 19.0 |
| 4 | Mineral oil | 53.5 | 57.0 | 59.0 |
| 5 | Olive fruit oil | 7.0 | 7.0 | 7.0 |
| 6 | L-carnitine | 0.5 | — | — |
| 7 | Hydrogenated C6-14 olefin polymer | 6.0 | 6.0 | 6.0 |
| 8 | Cyclodextrin | 0.4 | 0.4 | 0.4 |
| 9 | Ascorbyl palmitate | 0.3 | 0.3 | 0.3 |
| 10 | Tocopherol | 0.3 | 0.3 | 0.3 |

(Method for Producing Transdermal Absorption Preparation)

First, among the components present in Table 1 other than the lipophilic component, the lipophilic component and components added if necessary were each mixed with and dispersed in the lipophilic component to prepare a mixed solution constituting the adhesive layer. This mixed solution was mixed with or dispersed in a solvent such as acetone to prepare a coating liquid for adhesive layer formation.

This coating liquid was applied to a nonwoven fabric having a thickness of 250 µm as a support using a commercially available die coater so as to have a thickness of 250 µm, then a PET sheet having a thickness of 100 µm as a release sheet was pressure-bonded thereto, drying was performed at 60° C. for 8 hours to scatter the solvent, and then the resultant was cut into a size of 110 mm×135 mm (the four corners were rounded as illustrated in FIG. 1) to obtain a transdermal absorption preparation.

Test Example 1

Examination of Stability:

The obtained transdermal absorption preparations of Example 1 and Example 2 were placed in a thermostatic bath at a temperature of 50° C. and subjected to the examination of stability (changes in appearance, color, and smell). Incidentally, the standing period was set to two weeks. Abnormal changes were not observed from the transdermal absorption preparations after two weeks, and the stability of the transdermal absorption preparations was favorable.

Test Example 2

Examination of Fat Decreasing Effect of Transdermal Absorption Preparation:

The obtained transdermal absorption preparations of Example 1 and Example 2 were pasted to the left and right sides of the navel of the subjects (eight women for each (subjects 1 to 8 for Example 1 and subjects 9 to 16 for Example 2), and the age of subjects are presented in Table 2) by two sheets in the direction in which the long side was the vertical and the short side was the horizontal. The pasting was performed (7 to 8 hours of pasting time) during the bedtime of subjects, and the transdermal absorption preparations were continuously used for one week in this manner. The presence or absence of fat decreasing effect was examined by comparing the measurement results at the "(1) Upper circumference of navel" and "(2) Subcutaneous fat (area)" before and after use to each other. The results are presented in Table 2 ("1" in "Difference" in Table 2 indicates that the value after the test is lower than that before the test (the difference is minus)).

Incidentally, the measurement in (1) was performed using a commercially available tape measure (measure) (the unit of measurement was cm). Moreover, the measurement in (2) was performed (the unit of area was cm$^2$) based on the images attained using an abdominal tomographic image measurement/whole body X-ray CT scanner "Asteion (registered trademark) Super4" (manufactured by Toshiba Medical Systems Corporation).

(Evaluation Results)

TABLE 2

| Example 1 | | Upper circumference of navel (cm) | | | Subcutaneous fat (area: cm$^2$) | | |
|---|---|---|---|---|---|---|---|
| Subject | Age (years) | Before test | After test | Difference | Before test | After test | Difference |
| 1 | 39 | 84.0 | 78.0 | ▲ 6.0 | 211.2 | 190.1 | ▲ 21.1 |
| 2 | 55 | 84.0 | 78.1 | ▲ 5.9 | 241.5 | 225.3 | ▲ 16.2 |
| 3 | 43 | 80.8 | 75.8 | ▲ 5.0 | 202.7 | 190.6 | ▲ 12.1 |
| 4 | 26 | 76.1 | 72.3 | ▲ 3.8 | 191.7 | 180.3 | ▲ 11.4 |
| 5 | 36 | 74.6 | 71.0 | ▲ 3.6 | 108.1 | 97.3 | ▲ 10.8 |
| 6 | 21 | 79.2 | 76.1 | ▲ 3.1 | 257.5 | 238.6 | ▲ 18.9 |
| 7 | 68 | 88.4 | 85.4 | ▲ 3.0 | 232.1 | 224.0 | ▲ 8.1 |
| 8 | 26 | 70.2 | 68.2 | ▲ 2.0 | 134.2 | 130.1 | ▲ 4.1 |

| Example 2 | | Upper circumference of navel (cm) | | | Subcutaneous fat (area: cm$^2$) | | |
|---|---|---|---|---|---|---|---|
| Subject | Age (years) | Before test | After test | Difference | Before test | After test | Difference |
| 9 | 35 | 70.0 | 68.2 | ▲ 1.8 | 96.4 | 95.1 | ▲ 1.3 |
| 10 | 46 | 72.5 | 71.2 | ▲ 1.3 | 179.2 | 177.3 | ▲ 1.9 |
| 11 | 33 | 77.0 | 75.8 | ▲ 1.2 | 174.2 | 173.9 | ▲ 0.3 |
| 12 | 40 | 75.5 | 74.5 | ▲ 1.0 | 155.5 | 155.2 | ▲ 0.3 |
| 13 | 32 | 70.9 | 70.4 | ▲ 0.5 | 203.3 | 207.0 | 3.7 |
| 14 | 55 | 96.9 | 96.5 | ▲ 0.4 | 278.9 | 280.0 | 1.1 |
| 15 | 52 | 83.8 | 83.6 | ▲ 0.2 | 247.3 | 259.8 | 12.5 |
| 16 | 38 | 89.8 | 89.8 | 0 | 269.8 | 273.0 | 3.2 |

As presented in Table 2, it has been confirmed that the transdermal absorption preparations of Example 1 and Example 2 both have a fat decreasing effect and the transdermal absorption preparation of Example 1 having a higher content of phosphatidylcholine was briefly superior in fat decreasing effect (Example 2 exhibited the effect in (1) but a result equal to that of Example 1 was not attained in (2), and the results of Example 1 were superior to those of Example 2).

INDUSTRIAL APPLICABILITY

The present invention can be advantageously used as a means for providing a patch-type transdermal absorption preparation (phosphatidylcholine transdermal absorption preparation) which contains phosphatidylcholine as an active component in an adhesive layer and has a fat decreasing effect and has high industrial applicability.

REFERENCE SIGNS LIST

1 Transdermal absorption preparation (phosphatidylcholine transdermal absorption preparation)
2 Support
3 Adhesive layer
4 Release sheet
41 Cut (slit)

The invention claimed is:

1. A transdermal absorption preparation comprising:
a support; and
an adhesive layer formed on at least one side of the support;
wherein the adhesive layer contains a phosphatidylcholine;
carnitine;
20.0% to 35.0% by mass with respect to the entire adhesive layer of a thermoplastic elastomer; and
30.0% to 75.0% by mass with respect to the entire adhesive layer of a lipophilic component;
wherein an entire mass of the adhesive layer is 100% by mass; and
wherein a content of carnitine ranges from 8.5 to 12.0 parts by mass with respect to 100 parts by mass of phosphatidylcholine.

2. A transdermal absorption preparation comprising:
a support; and
an adhesive layer formed on at least one side of the support;
wherein the adhesive layer contains phosphatidylcholine, carnitine;
20.0% to 35.0% by mass with respect to the entire adhesive layer of a thermoplastic elastomer; and
30.0% to 75.0% by mass with respect to the entire adhesive layer of a lipophilic component;
wherein an entire mass of the adhesive layer is 100% by mass; and
further comprising a branched polyolefin.

3. The transdermal absorption preparation according to claim 2, wherein the branched polyolefin is a hydrogenated C6-14 olefin polymer.

4. A transdermal absorption preparation comprising:
a support;
an adhesive layer formed on at least one side of the support;
wherein the adhesive layer contains phosphatidylcholine; carnitine;
a styrene-based thermoplastic elastomer in an amount of from 20.0% to 35.0% by mass with respect to the entire adhesive layer; and
30.0% to 75.0% by mass with respect to the entire adhesive layer of a lipophilic component;
wherein an entire mass of the adhesive layer is 100% by mass; and
wherein a content of carnitine ranges from 8.5 to 12.0 parts by mass with respect to 100 parts by mass of phosphatidylcholine.

5. The transdermal absorption preparation according to claim 1, wherein a content of phosphatidylcholine is 2.5% to 8.0% by mass with respect to an entire adhesive layer.

6. The transdermal absorption preparation according to claim 4, wherein a content of phosphatidylcholine is 2.5% to 8.0% by mass with respect to an entire adhesive layer.

7. The transdermal absorption preparation according to claim 1, wherein the lipophilic component contains mineral oil.

8. The transdermal absorption preparation according to claim 4, wherein the lipophilic component contains mineral oil.

9. The transdermal absorption preparation according to claim 5, wherein the lipophilic component contains mineral oil.

10. The transdermal absorption preparation according to claim 6, wherein the lipophilic component contains mineral oil.

* * * * *